(12) United States Patent
Goebel et al.

(10) Patent No.: US 6,433,334 B1
(45) Date of Patent: Aug. 13, 2002

(54) ION MOBILITY SPECTROMETER

(75) Inventors: Johann Goebel; Ulrich Breit, both of Munich (DE)

(73) Assignee: Eads Deutschland GmbH, Ottobrunn (DE)

( * ) Notice: Subject to any disclaimer, the term of this patent is extended or adjusted under 35 U.S.C. 154(b) by 0 days.

(21) Appl. No.: 09/647,997
(22) PCT Filed: Apr. 1, 1999
(86) PCT No.: PCT/DE99/00992
  § 371 (c)(1),
  (2), (4) Date: Oct. 10, 2000
(87) PCT Pub. No.: WO99/51978
  PCT Pub. Date: Oct. 14, 1999

(30) Foreign Application Priority Data
  Apr. 7, 1998 (DE) .......................... 198 15 435
(51) Int. Cl.$^7$ .......................... H01J 49/40; B01D 59/44
(52) U.S. Cl. .................. 250/286; 250/288; 250/283; 250/282
(58) Field of Search ................ 250/286, 288, 250/282, 283

(56) References Cited

U.S. PATENT DOCUMENTS

| | | | |
|---|---|---|---|
| 4,390,784 A | 6/1983 | Browning et al. | 250/287 |
| 4,724,394 A | 2/1988 | Langer et al. | 324/464 |
| 4,777,363 A | 10/1988 | Eiceman et al. | 250/286 |
| 5,420,424 A | 5/1995 | Carnhan et al. | 250/287 |
| 5,965,882 A | * 10/1999 | Megerle et al. | 250/287 |
| 5,998,788 A | * 12/1999 | Breit | 250/286 |

FOREIGN PATENT DOCUMENTS

| | | |
|---|---|---|
| DE | 1 591 345 | 12/1970 |
| DE | 41 34 212 A1 | 4/1993 |
| GB | 1105604 | 3/1965 |
| GB | 2 198 579 A | 6/1987 |
| GB | 2 255 671 A | 11/1992 |

* cited by examiner

Primary Examiner—Bruce Anderson
Assistant Examiner—Nikita Wells
(74) Attorney, Agent, or Firm—Crowell & Moring LLP

(57) ABSTRACT

In an ion mobility spectrometer, especially a miniaturized ion mobility spectrometer, the potential-conducting surfaces of the ion collector and ion gate form an angle less than 90° with the drift chamber axis. This makes it possible to provide openings in the face of the drift chamber for the required purge gas supply without limiting the size of the potential-conducting surface.

7 Claims, 2 Drawing Sheets

ION MOBILITY SPECTROMETER

Figure 1:
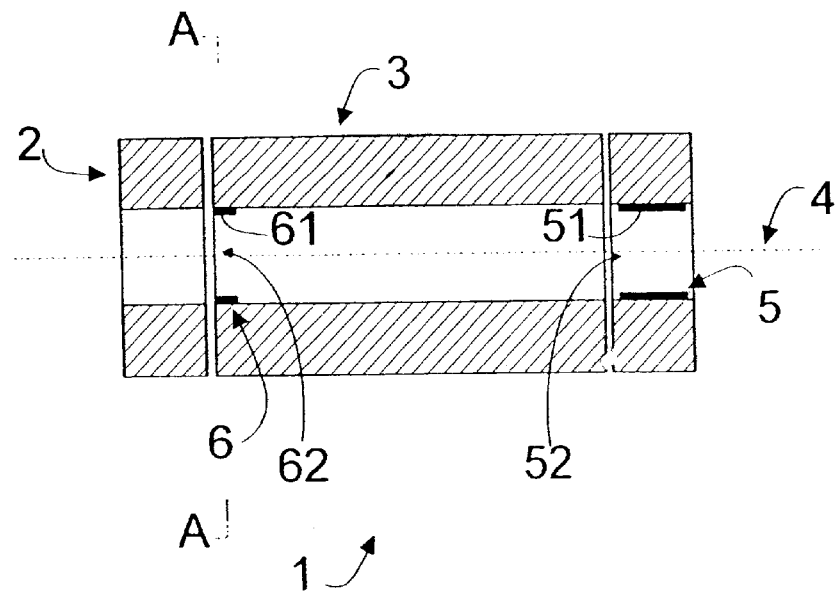

The invention concerns an ion mobility spectrometer according to the preamble of claim 1.

There is an example of a prior-art ion mobility spectrometer of the cited kind in DE 15 91 345.9 or U.S. Pat. No. 4,390,784. Such an ion mobility spectrometer can detect even small portions of substances to be analysed in a carrier gas and usually consists of an ionisation chamber in which the molecules of the substance to be analysed and the carrier gases are ionised. Connected to this ionisation chamber is a drift chamber. The ions enter it via an electrically switchable ion gate. Between the ion gate and an ion collector on the opposite end of the drift chamber is an axially aligned electrical field. The ions formed in the ionisation chamber move along the drift path in the field toward the ion collector. The ion gate is switched so that it lets a swarm of the ion mixture which is to be analysed into the drift chamber. While drifting toward the ion collector, this swarm is divided into partial swarms that are characteristic for the components of the mixture. The ions are neutralized on the conductor surface of the ion collector, and their charge is released. This is also described as ion discharging on a potential-conducting surface. The partial swarms contact the ion collector at different times and are detected by means of signal electronics. The received signal allows conclusions to be drawn about the analysed mixture.

U.S. Pat. No. 4,777,363 discloses the ion gate as an arrangement of parallel wires that run perpendicular to the drift axis. All even wires are electrically connected to each other, and all uneven wires are electrically connected to each other. Between the two wires groups obtained in this manner, a voltage is applied to block the ion gate which is known in the literature as a Bradburry-Nielson arrangement. If the two wire groups are at the same potential, the gate is opened to the ions. If a voltage is applied between them, the ions are led to the grid wires where they release their charges. To reduce the influence of mirror charges, this device also uses an aperture grid in front of the ion collector; however, ions are lost by being discharged there.

U.S. Pat. No. 4,390,784 discloses an ion collector at the end of the drift path that is perpendicular to the drift axis and whose ion-discharging surface extends nearly over the entire cross-section of the drift chamber.

A purge gas such as nitrogen or air usually flows through the drift chamber. U.S. Pat. No. 4,390,784 has a feed for the purge gas at the downstream end of the drift chamber and a drain at the upstream end of the drift chamber. Since the purge gas has to be guided past the collector, it cannot cover the entire cross-section of the drift chamber. In the prior-art devices, however, only a small percent of the collector surface is lost from the gas flow since the gas flow is typically ⅛ or ⅙ inch, and the drift chamber cross-section is 1–2 cm (U.S. Pat. No. 4,390,784).

If, however, one wishes to miniaturize the cross-section of an ion mobility spectrometer, the surface loss due to the gas flow is a problem. A similar problem arises with the ion gate in the miniaturization of ion mobility spectrometers. A conventional Bradburry-Nielson wire grid is difficult to miniaturize since a sufficient number of grid wires cannot be placed in the miniaturized cross-section with the given wire thickness.

It is therefore the task of the present invention to create an ion mobility spectrometer that is suitable for miniaturization.

The cited problem is solved with the features of patent claim 1. Advantageous developments are characterized in the subcdaims. According to the invention, the potential-conducting surface of the ion gate or ion collector forms an angle with the drift chamber axis that is much less than 90°. This makes it possible to provide the required openings in the faces of the drift chamber to feed and remove the purge gas without limiting the size of the potential-conducting surface. This allows the cross-section of the ion mobility spectrometer to be miniaturized. In addition, the above-cited aperture grid can be dispensed with since the effect of influence charges of the ion swarm is much less due to the small cross-sectional surface of the ion collector in the drift axis direction.

The ion-discharging surface of the collector can of course be composed of several sections that are electrically connected to each other or are connected directly to the signal detecting electronics. Since the ion-discharging surfaces form an angle less than 90° with the drift chamber axis, there remains space for an opening for a gas flow in a central, inner radial area of the drift chamber. The collector surface therefore encloses the gas flow.

Since the surface of the ion gate forms an angle much less than 90° with the drift chamber axis, the gas can flow unhindered through it like at the ion collector.

It is in particular possible to place the potential-conducting surface of the ion gate and the ion collector inside on the drift chamber wall. In certain cases, an insulating layer must be between the potential-conducting surface and the inner wall of the drift chamber.

In a preferred embodiment, the size of the potential-conducting surface of the ion collector is about the same of the opening perpendicular to the drift direction through which the drifting purge gas is guided to allow the collector to collect all the ions at the end of the drift path.

Figure 2:
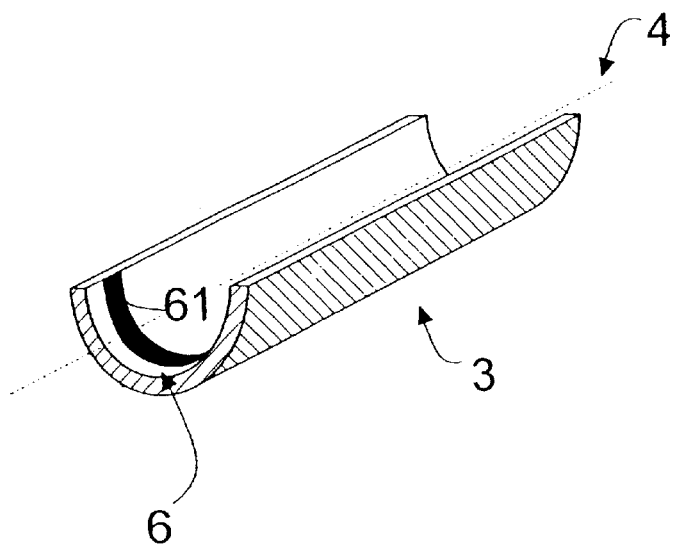
Figure 3:
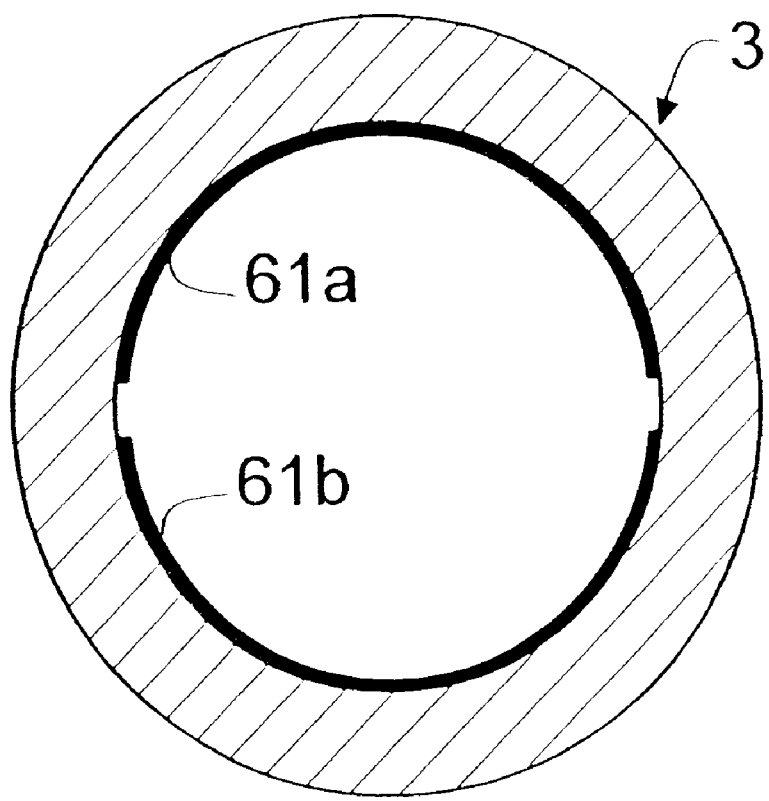

Exemplary embodiments of the invention will be described in the following with reference to a drawing. Shown are:

FIG. 1 a simplified lengthwise section of an ion mobility spectrometer;

FIG. 2 a perspective view of a cut-away drift chamber of the ion mobility spectrometer in FIG. 1; and FIG. 3 a section of the ion mobility spectrometer from FIG. 1 along line A—A in an embodiment slightly altered from FIG. 2.

FIG. 1 shows a lengthwise section of an ion mobility spectrometer 1. It has an ionisation chamber 2 in which an analytical substance mixture is ionised to form a gaseous ion mixture. Communicating with this ionisation chamber 2 is an ion gate 6 that has a potential-conducting surface 61 designed as a conductive strip. The potential-conducting surface 61 is annular so that is has a central opening 62. The ion gate 6 can switch between a blocked and open state to briefly let a swarm of the ion mixture through the opening 62 onto a subsequent drift path.

The drift path is formed by a drift chamber 3 in which an electrical field is injected along the drift chamber axis 4. Ions that move in this electrical field travel at different rates along the drift path depending on their own ion mobility. At the end of the drift path is an ion collector 5 with a potential-conducting surface 51 designed as a conductive strip. The potential-conducting surface 51 is on the inner wall of the drift chamber 3 in the shape of a ring so that is has a central opening 62. The ion collector 5 is connected to a signal electronics system (not shown). Ions that contact the potential-conducting surface 51 of the ion collector 5 generate a signal current there that is amplified and evaluated by the signal electronics. The arrangement of ionisation chamber 2, ion gate 6, drift chamber 3 and ion collector 5 is purged by a drift gas by means of a purge gas device (not shown). This drift gas flows through the collector opening 52 at the downstream end, flows through the drift chamber 3, passes through the opening 62 of the ion gate 6 and is removed from the system.

When the ion gate 6 is closed, all of the ions generated in the ionisation chamber 2 flow past the potential-conducting surface 61 of the ion gate 6. The ion gate 6 is closed by switching the potential-conducting surface 61 e.g. to zero potential. The ions of the ion mixture formed in the ionisation chamber 2 cannot pass along the drift path since the potential-conducting surfaces 61 of the ion gate 6 represent an insuperable potential barrier. The ion gate 6 can be opened by switching its potential-conducting surface 61 to the potential of the drift field at this place. The ions can pass through the ion gate 6 and follow the electrical drift field to the ion collector that runs along the drift chamber axis 4.

To separate the mixture into partial swarms, a single swarm with an ion mixture islet into the drift chamber 3 at the upstream end, that is, at the start of the drift path. The ion gate 6 is opened and closed on a particular schedule by an electronic circuit (not shown). The swarm with the ion mixture drifts under the influence of the electrical field to the ion collector 5 and is divided into partial swarms with the components of the mixture. The separation occurs according to the ion mobility. At the end of the drift chamber 3, the individual ions are collected at the ion-discharging surfaces 51 of the ion collector 5, and the current is fed to the signal electronics (not shown).

Since the opening 52 for the supply of the drift gas is centrally located close to the drift chamber axis, it does not limit the size of the ion-discharging surface 51 of the ion collector 5. This makes it possible to miniaturize the cross-section of the ion mobility spectrometer.

To prevent ions from passing the ion-discharging surface 51 without being measured at the ion-discharging surface 51, the width of the annular ion-discharging surface 51 in the drift direction is about the same as the diameter of the opening 52 in a preferred embodiment. This ensures that basically all the field lines of the drift field end at the ion-discharging surface 51 that is at reference potential, and all the ions introduced in the drift path are collected on the ion-discharging surface 51.

As can easily be seen, ions that pass through the drift chamber close to the drift chamber axis 4 have a longer path to the ion-discharging surface 51 of the collector on the drift chamber inner wall than axially distant ions. This causes ions of the same substance that have begun to travel along the drift path at the same time to contact the ion-discharging surface 51 of the collector 5 at different times. The time difference increases with the difference in the path length between axially close and axially distance ions. The diameter of the drift chamber is below 5 mm for miniaturized ion mobility spectrometers for which the ion gate and collector arrangement according to the invention is particularly suitable so that the difference-in path lengths and hence the time differences are not that important.

FIG. 2 shows a perspective view of a section of a drift chamber 3 from FIG. 1. The ion gate 6 is formed at the front end together with the annular potential-conducting surface 61.

FIG. 3 shows a section along line A—A of FIG. 1 of an ion gate 6 altered slightly from FIG. 2. The ion gate 6 in FIG. 3 has two potential-conducting sections 61a and 61b in contrast to FIG. 2. These sections 61a and 61b correspond to the annular surface 61 from FIG. 2 with the difference that they are divided at two places. Between the half rings obtained in this manner, voltage is applied from an electronic circuit (not shown) to block the ion gate. This voltage perpendicular to the direction of the drift field penetrates the ions formed in the ionisation chamber 2 to the potential-conducting sections 61a and 61b. To open the ion gate 6, the sections 61a, 61b are switched to the potential of the drift field at the potential-conducting sections. The ions do not encounter a drop in potential or a transverse field and can pass through the ion gate 6.

For the sake of illustration, a circular cross-section for the drift chamber was assumed in the exemplary embodiments from FIGS. 1 and 2. According to the doctrine of the invention, the drift chamber cross-section can also have other shapes, especially rectangular, slot-like or polygonal.

What is claimed is:

1. An ion mobility spectrometer comprising:

an ionization chamber for ionizing a substance to form a gaseous ion mixture;

an ion gate that can be electrically switched between blocked and open states to briefly pass a quantity of the ion mixture along a drift path;

a drift chamber forming the drift path with an electrical drift field running along a drift chamber axis in which the ions of the ion mixture are separated according to their ion mobility; and an ion collector connected with signal electronics to detect separated ions, both the ion gate and the ion collector having a potential-conducting surface; wherein at least one of the following is true:

the potential-conducting surface of the ion gate is on at least one wall between the ionization and drift chambers and runs substantially parallel to said at least one wall; and the potential-conducting surface of the ion collector is on at least one wall of the drift chamber and runs substantially parallel to said at least one wall.

2. An ion mobility spectrometer according to claim 1, wherein the size of the potential-conducting surfaces in the drift direction is approximately the same as an opening perpendicular to the drift direction.

3. An ion mobility spectrometer according to claim 1, wherein the potential-conducting surface of at least one of the ion gate and ion collector is directly adjacent or on the drift chamber wall.

4. An ion mobility spectrometer according to claim 1, wherein the potential-conducting surface of at least one of the ion gate and ion collector is annular.

5. An ion mobility spectrometer according to claim 1, wherein the potential-conducting surface of at least one of the ion gate and ion collector comprises at least two sections that are diametrically opposed along the drift chamber axis.

6. An ion mobility spectrometer according to claim 5, wherein a potential is applied to the potential-conducting sections of the ion gate to close the ion gate that is above or below the maximum potential of the drift area.

7. An ion mobility spectrometer according to claim 1, wherein a potential is applied to the potential-conducting surface of the ion gate to close the ion gate, which potential is substantially different from the potential of the drift field at the potential-conducting surface.

* * * * *